United States Patent
Ouyang et al.

(10) Patent No.: US 7,419,298 B2
(45) Date of Patent: Sep. 2, 2008

(54) THERMAL IMAGING METHOD AND APPARATUS

(75) Inventors: Zhong Ouyang, Glastonbury, CT (US); Kevin D. Smith, Glastonbury, CT (US)

(73) Assignee: United Technologies Corporation, Hartford, CT (US)

(*) Notice: Subject to any disclaimer, the term of this patent is extended or adjusted under 35 U.S.C. 154(b) by 99 days.

(21) Appl. No.: 11/135,896

(22) Filed: May 24, 2005

(65) Prior Publication Data

US 2007/0036199 A1  Feb. 15, 2007

(51) Int. Cl.
*G01N 25/72* (2006.01)
*G01K 1/02* (2006.01)

(52) U.S. Cl. .............. 374/5; 374/7; 374/120; 250/330; 250/341.6

(58) Field of Classification Search ........ 374/4–7, 374/57, 43–44, 120–124, 130, 137; 250/330, 250/332, 338.1, 341.6
See application file for complete search history.

(56) References Cited

U.S. PATENT DOCUMENTS

| | | | | |
|---|---|---|---|---|
| 3,672,204 | A | * | 6/1972 | Green ................ 374/43 |
| 5,111,048 | A | * | 5/1992 | Devitt et al. .......... 250/342 |
| 5,287,183 | A | * | 2/1994 | Thomas et al. ........ 348/571 |
| 5,292,195 | A | * | 3/1994 | Crisman, Jr. .......... 374/4 |
| 5,582,485 | A | * | 12/1996 | Lesniak ................ 374/5 |
| 6,364,524 | B1 | * | 4/2002 | Markham ............. 374/131 |
| 6,367,968 | B1 | | 4/2002 | Ringermacher et al. |
| 6,394,646 | B1 | * | 5/2002 | Ringermacher et al. ... 374/7 |
| 6,437,334 | B1 | * | 8/2002 | Thomas et al. ........ 250/341.6 |
| 6,542,849 | B2 | | 4/2003 | Sun |
| 6,712,502 | B2 | | 3/2004 | Zalameda et al. |
| 6,751,342 | B2 | * | 6/2004 | Shepard ............... 382/141 |
| 7,018,094 | B1 | * | 3/2006 | Bates ................... 374/121 |
| 7,044,636 | B2 | * | 5/2006 | Taketoshi et al. ....... 374/45 |
| 7,199,366 | B2 | * | 4/2007 | Hahn et al. ............ 250/330 |
| 7,365,330 | B1 | * | 4/2008 | Sun .................... 250/341.6 |

(Continued)

FOREIGN PATENT DOCUMENTS

GB  2164147 A  *  3/1986

OTHER PUBLICATIONS

Zhong Ouyang et al., Progress in the Rapid, Contactless Measurement of Thermal Diffusivity, Review of Progress in Quantitative NDE, vol. 18, New York, 1999, pp. 627-629.

(Continued)

*Primary Examiner*—Gail Verbitsky
(74) *Attorney, Agent, or Firm*—Bachman & LaPointe, P.C.

(57) ABSTRACT

An inspection apparatus includes a light source positioned to direct light to a first surface of a workpiece. An infrared detector is positioned to receive radiation from the first surface. A data acquisition and processing computer is coupled to the light source and the infrared detector. The computer triggers the light source to emit the light a number of instances. The computer acquires thermal data from the infrared detector for a number of times after each of the instances. The computer is configured to process the data using a theoretical solution to analyze the thermal data based upon an average of the thermal data for a number of each of corresponding ones of the times from different ones of the instances.

22 Claims, 4 Drawing Sheets

U.S. PATENT DOCUMENTS

| | | | |
|---|---|---|---|
| 2002/0110176 A1* | 8/2002 | Sun et al. ........................ | 374/5 |
| 2003/0219059 A1* | 11/2003 | Scott .............................. | 374/5 |
| 2004/0247192 A1* | 12/2004 | Kajiki et al. ................. | 382/239 |
| 2005/0002546 A1* | 1/2005 | Florent et al. ................ | 382/128 |
| 2006/0262971 A1* | 11/2006 | Foes et al. ................... | 382/141 |

OTHER PUBLICATIONS

Zhong Ouyang et al., Novel Measurement of Anisotropic Thermal Diffusivity, Review of Progress in Quantitative NDE, vol. 17, New York, 1998, pp. 453-456.

J.P. Feist et al., Phosphor Thermometry for High Temperature Gas Turbine Applications, Instrumentation in Aerospace Simulation Facilities, Jun. 1999, pp. 6.1-6.7.

Steven M. Shepard et al., Reconstruction and Enhancement of Active Thermographic Image Sequences, Optical Engineering SPIE, May 2003, pp. 1337-1342, vol. 42, No. 5.

* cited by examiner

THERMAL IMAGING METHOD AND APPARATUS

BACKGROUND OF THE INVENTION

The invention relates to thermal imaging. More particularly, the invention relates to flash thermal imaging.

Flash thermal imaging inspection methods and apparatus are shown in U.S. Pat. Nos. 6,542,849 and 6,712,502 (the '849 and '502 patents respectively, the disclosures of which are incorporated by reference herein as if set forth at length). A basic thermal imaging system includes a light source (e.g., one or more flash lamps) and a detector (e.g., an infrared imaging camera). The source and detector are coupled to a control system to control inspection of a workpiece. After a flash from the source illuminates a surface of the workpiece, the detector is used to obtain a time series of readings or images of light radiated from the surfaces. The decay properties of such radiated light may be used to evaluate the workpiece. Such techniques may be used to evaluate material thickness, the presence of defects in the material, and the like.

SUMMARY OF THE INVENTION

One aspect of the invention involves an inspection apparatus includes a light source positioned to direct light to a first surface of a workpiece. An infrared detector is positioned to receive radiation from the first surface. A data acquisition and processing computer is coupled to the light source and the infrared detector. The computer triggers the light source to emit the light a number of instances. The computer acquires thermal data from the infrared detector for a number of times after each of the instances. The computer is configured to process the data using a theoretical solution to analyze the thermal data based upon an average of the thermal data for a number of each of corresponding ones of the times from different ones of the instances The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
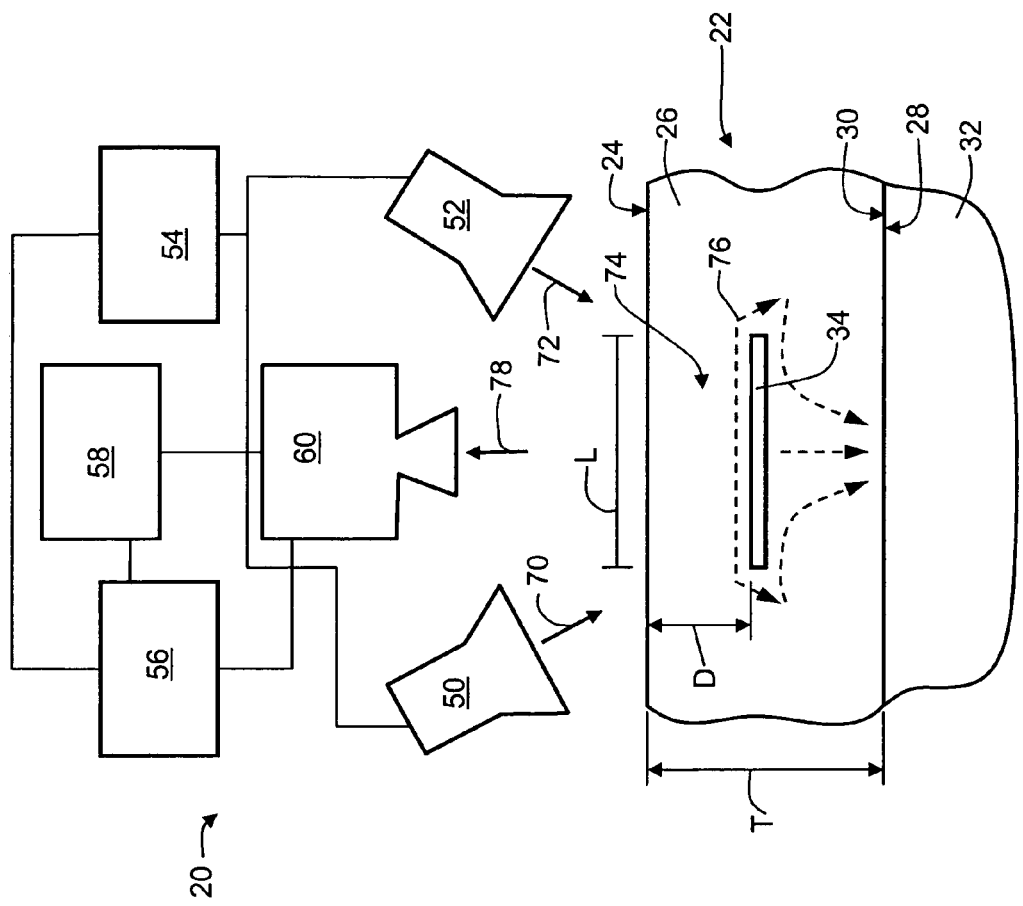
FIG. 1 is a schematic view of a thermal imaging system.

FIG. 1 shows thermal imaging system 20. The illustrated system 20 may be similar to that of the '849 patent except as is described below. Yet other systems may be used. The system 20 may be used to inspect a workpiece 22. The workpiece 22 has at least one exposed (outer) surface 24. The exemplary surface 24 is an exterior surface of a surface layer 26. The surface layer 26 has an interior surface 28 atop the exterior surface 30 of a substrate 32. An exemplary such layer and substrate combination involves a metallic alloy substrate 32 and a protective coating layer 26.

The system 20 may be used to detect the presence of a defect 34 in the layer 26. The exemplary defect 34 may be a void at a depth D below the surface 24 and having a characteristic transverse dimension L. The system may further be used to determine the position (e.g., D), size (e.g., L and/or a defect thickness), or other properties of the defect 34. Alternatively, the system may be used to determine a thickness T of the layer 26.

The system 20 includes first and second flash lamps 50 and 52. In the exemplary system, the lamps 50 and 52 are commonly powered by a power supply 54 for simultaneous operation. Alternatively, the lamps could be powered by separate power supplies, synchronized by a control system (e.g., a computer). The supply 54 is, in turn, connected to the control system which may include the combination of a data acquisition and processing unit 56 and a function generator 58. The unit 56 and generator 58 are also coupled to an infrared imaging camera 60.

The lamps 50 and 52 are positioned to direct flashes of light 70 and 72 to the surface 24. The light locally heats the workpiece 22. A region 74 between the defect 34 and surface 24 may be heated differently and may cool differently than regions beyond the defect. The defect may hinder heat flux 76 from the region 74 deeper into the workpiece. Thus, the region 74 may become hotter than a similar surface region beyond the defect. Other properties may also be affected. Depending upon the property of the material of the layer 26 and the nature of the defect, the defect might be more conductive thereby reversing the effects.

Figure 2:
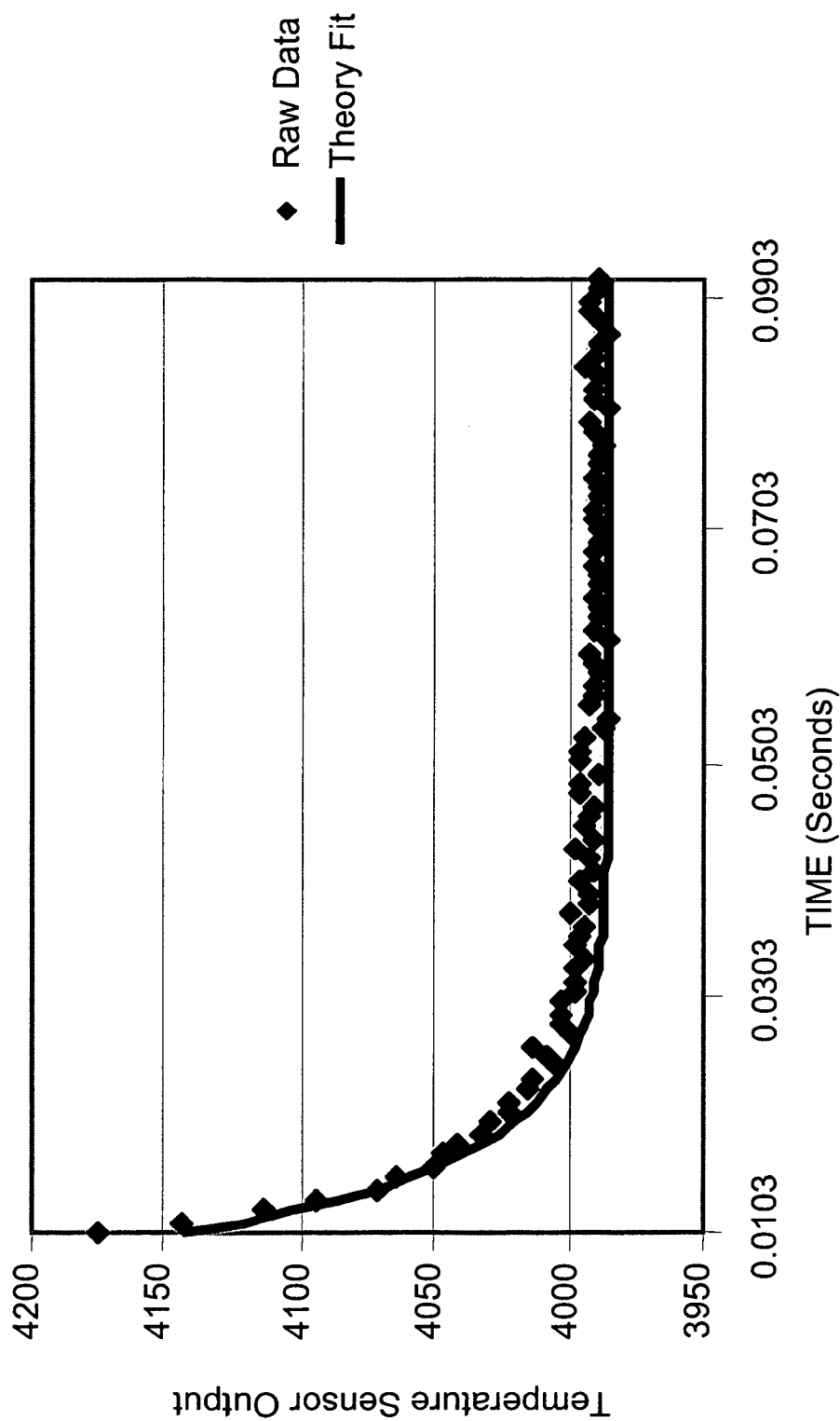
FIG. 2 is a plot of raw detector data and a theoretical fit for a prior art system and method.

After the flashes of light 70 and 72, the workpiece radiates energy from its surface 24. The lens of the camera 60 is positioned to receive returned radiated light 78 from the surface 24 (e.g., infrared light). The output of the camera 60 may be representative of temperature. FIG. 2 shows digital counts outputted by the camera 60 inspecting the layer 26 at the defect. This output is proportional to temperature. The horizontal axis shows the time in seconds after the flash of the lamps. The vertical axis shows temperature sensor output (raw and not converted to any particular temperature scale). FIG. 2 further shows a theoretical fit to this raw data. The fit was calculated based upon a theoretical temperature-time function:

$$T(t) = \frac{1}{\sqrt{\pi \alpha \cdot t}} \sum_{n=-\infty}^{\infty} e^{-\frac{n^2 d^2}{\alpha \cdot t}}$$

where T is temperature, t is time, $\alpha$ is the thermal diffusivity of the layer 26, and d is a local effective surface thickness of the material in the layer (T away from the defect and D along the defect). Because T is larger than D, it will take longer time for the heat reach the interior surface 28 and reflect back to the exposed surface 24. For theoretical fitting, it may be advantageous to use a longer time use to obtain a fit away from the defect than along the defect. Different theoretical fittings are appropriate for different situations (e.g., different layer thicknesses and combinations, for determining particular layer thicknesses, and/or determining particular defects even in a given nominal combination, and the like).

Figure 3:
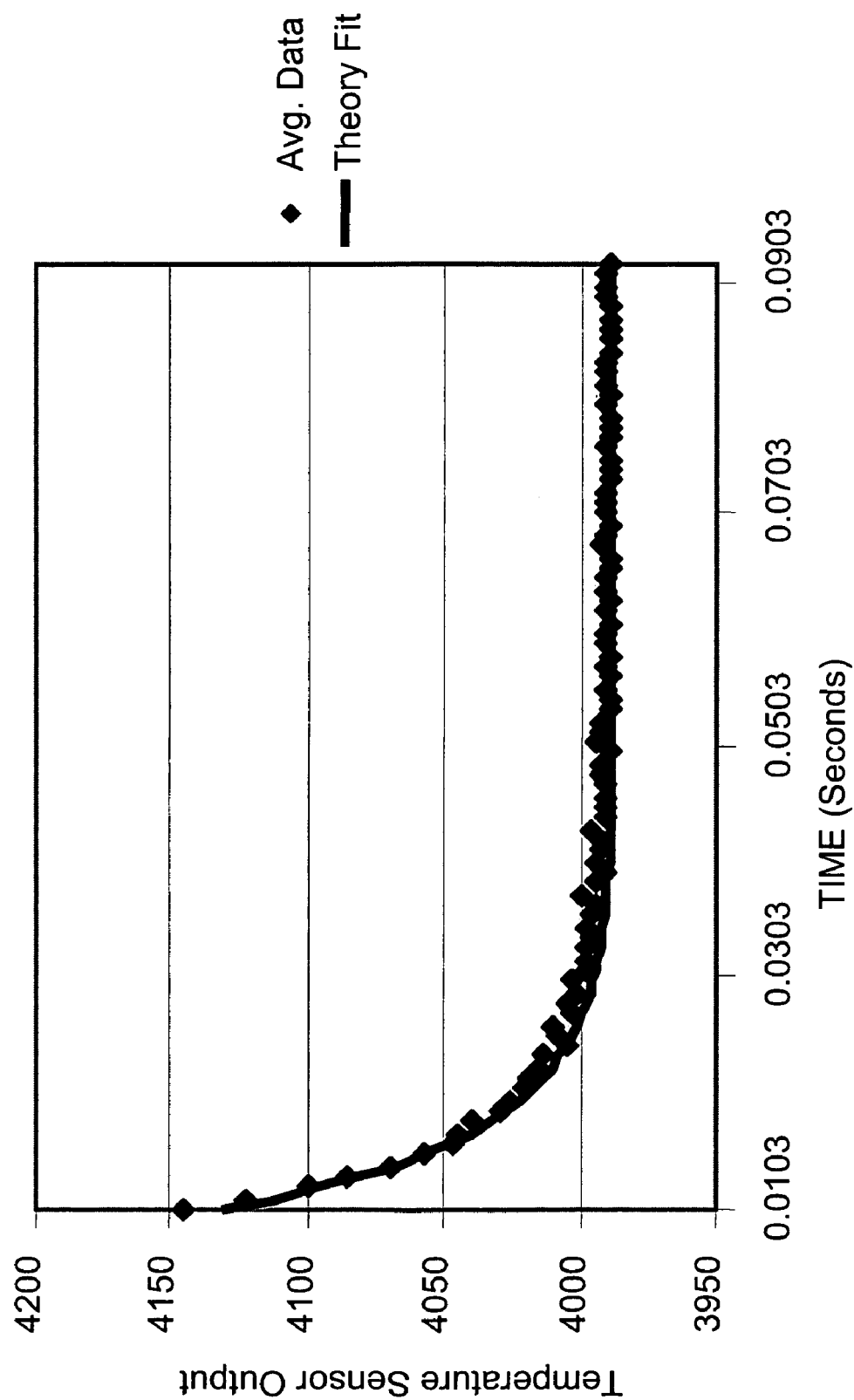
FIG. 3 is a plot of average data and a theoretical fit for a system and method according to the present invention.
Figure 4:
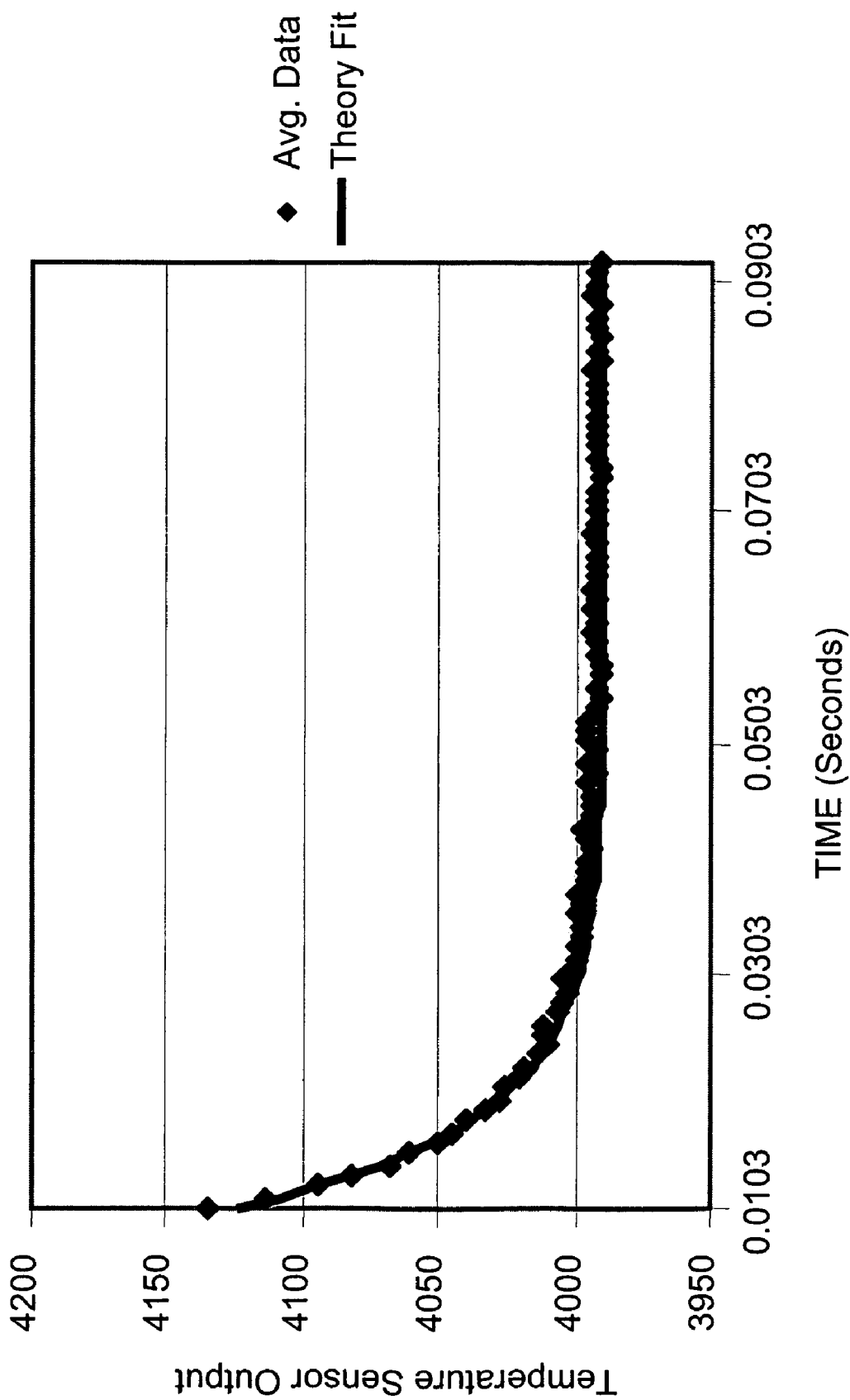
FIG. 4 is a plot of average data and a theoretical fit for a system and method according to the present invention.

Rather than fit to raw data, FIG. 3 shows data averaged for two flashes. FIG. 4 shows a similar average for four flashes. In each of these two situations, the theoretical fit more closely matches. The use of multiple flashes may be particularly significant for evaluating thicknesses of and defects in thin layers and walls. For example, in evaluating a thin wall or finding a shallow defect, a very short duration pulse may be appropriate. A baseline level of noise (e.g., due to random and environmental factors) may be sufficiently large relative to the detected radiation so as to render inaccurate single flash data. Thus, depending upon the particular situation, the control system may be programmed or adjusted to provide a combination of flash brevity and a larger number of flashes to improve accuracy.

This use of averaged data may be implemented in the remanufacturing or reengineering of an existing thermal imaging system. For example, at one level this may be implemented by a software change.

One or more embodiments of the present invention have been described. Nevertheless, it will be understood that various modifications may be made without departing from the spirit and scope of the invention. For example, when implemented in a reengineering or remanufacturing situation, details of the existing system will influence or dictate details of the implementation. Furthermore, the principles may be combined with other techniques whether known or yet-developed. Accordingly, other embodiments are within the scope of the following claims.

What is claimed is:

1. An inspection apparatus comprising:
    a light source positioned to direct light to a first surface of a workpiece and consisting essentially of a pair of flash lamps positioned at a first side of the workpiece;
    an infrared detector comprising an infrared camera positioned near said first side to receive radiation from the first surface; and
    a data acquisition and processing computer:
        coupled to said light source for triggering said light source to emit said light a plurality of instances;
        coupled to said infrared detector for acquiring thermal data for a plurality of times after each of the instances; and
        configured for processing said thermal data by:
            for a plurality of each of corresponding ones of said times, averaging the thermal data from different ones of said instances; and
            using a theoretical solution to analyze said thermal data based upon said average, wherein the average is a separate average for each plurality of the corresponding times.

2. The apparatus of claim 1 wherein:
    said average comprises a mean.

3. The apparatus of claim 1 wherein:
    said average is taken across 2-20 of said instances.

4. The apparatus of claim 1 wherein:
    said average is taken across 3-10 of said instances.

5. The apparatus of claim 1 wherein:
    said average is taken across 2-4 of said instances.

6. The apparatus of claim 1 wherein:
    the data comprises image data.

7. The apparatus of claim 1 in combination with said workpiece, said workpiece being a gas turbine engine hollow cast component.

8. The apparatus of claim 1 in combination with said workpiece, said workpiece being a coated gas turbine engine component.

9. A method comprising:
    causing a light source to emit pulses of light a plurality of instances, said light impinging a first surface of a workpiece;
    acquiring thermal data for the workpiece first surface for a plurality of times after each of the instances; and
    processing said thermal data by:
        for a plurality of each of corresponding ones of said times, averaging the thermal data from different ones of said instances; and
        using a theoretical solution to analyze said thermal data based upon said average of said thermal data, wherein the average is a separate average for each plurality of the corresponding times.

10. The method of claim 9 wherein:
    said average is taken across 3-10 of said instances.

11. The method of claim 9 wherein:
    said average is taken across 2 of said instances.

12. The method of claim 9 used to measure a wall thickness of a gas turbine engine hollow cast component.

13. The method of claim 9 used to measure a coating thickness of a gas turbine engine component.

14. The method of claim 9 used to detect a defect in a coating of a gas turbine engine component.

15. An apparatus comprising:
    first means for directing light to a first surface of a workpiece;
    second means for receiving radiation from the first surface; and
    third means for:
        triggering said light source to emit said light a plurality of instances;
        for acquiring thermal data for a plurality of times after each of the instances; and
        for processing said thermal data using a theoretical solution to analyze said thermal data based upon an average of said thermal data for a plurality of each of corresponding ones of said times from different ones of said instances, wherein the average is a separate average for each plurality of the corresponding times.

16. The apparatus of claim 15 wherein:
    the third means is configured to take said average across 3-10 of said instances.

17. The apparatus of claim 15 wherein:
    the third means is configured to take said average as a mean.

18. A method for modifying a thermal imaging system from a baseline configuration having:
    a light source positioned to direct light to a first surface of a workpiece;
    an infrared detector positioned to receive radiation from the first surface; and
    a data acquisition and processing computer:
        coupled to said light source for triggering said light source to emit a flash of said light;
        coupled to said infrared detector for acquiring thermal data for a plurality of times after said flash; and
        configured for processing said thermal data using a theoretical solution to analyze said thermal data based upon said thermal data for a said flash, the method comprising:
    modifying the data acquisition and processing computer to or providing a replacement data acquisition and processing computer to:
        trigger said light source to emit a plurality of flashes of said light;
        acquire thermal data for a plurality of times after each of the flashes; and
        configured for processing said thermal data by:
            for a plurality of each of corresponding ones of said times, averaging the thermal data from different ones of said instances; and using a theoretical solution to analyze said thermal data based upon the average of said thermal data for a plurality of each of corresponding ones of said times from different ones of said flashes, wherein the average is a separate average for each plurality of the corresponding times.

19. The method of claim 18 wherein:

the data acquisition and processing computer is configured in the modified system to take said average as a mean across 3-10 of said instances.

20. The method of claim 18 wherein the data acquisition and processing computer is configured in the modified system to take said average as a mean.

21. The method of claim 18 wherein:

the data acquisition processing computer is configured in the baseline system to analyze said thermal data based upon said thermal data for only a single said flash; and the data acquisition and processing computer is configured in the modified system to take said average as a mean across 2-4 of said instances.

22. An inspection apparatus comprising:

a light source positioned to direct light to a first surface of a workpiece and consisting and essentially of a pair of flash lamps positioned at a first side of the workpiece;

an infrared detector comprising an infrared camera positioned near said first side to receive radiation from the first surface; and a data acquisition and processing computer:
  coupled to said light source for triggering said light source to emit said light a plurality of instances;
  coupled to said infrared detector for acquiring thermal data for a plurality of times after each of the instances; and
  configured for processing said thermal data by:
    for a plurality of each of corresponding ones of said times, averaging the thermal data from 2-4 different ones of said instances; and
  using a theoretical solution to analyze said thermal data based upon said average, wherein the average is a separate average for each plurality of the corresponding times.

* * * * *

UNITED STATES PATENT AND TRADEMARK OFFICE
CERTIFICATE OF CORRECTION

PATENT NO.         : 7,419,298 B2                                          Page 1 of 1
APPLICATION NO.    : 11/135896
DATED              : September 2, 2008
INVENTOR(S)        : Zhong Ouyang et al.

It is certified that error appears in the above-identified patent and that said Letters Patent is hereby corrected as shown below:

In column 4, claim 11, line 12, delete "2" and insert --2-4--.

Signed and Sealed this

Seventeenth Day of November, 2009

David J. Kappos
*Director of the United States Patent and Trademark Office*